(12) United States Patent
Malek

(10) Patent No.: US 7,402,176 B2
(45) Date of Patent: Jul. 22, 2008

(54) INTERVERTEBRAL DISC PROSTHESIS

(76) Inventor: Michel H. Malek, 577 W. Hawthorne Pl., Chicago, IL (US) 60657

( * ) Notice: Subject to any disclaimer, the term of this patent is extended or adjusted under 35 U.S.C. 154(b) by 0 days.

(21) Appl. No.: 11/734,564

(22) Filed: Apr. 12, 2007

(65) Prior Publication Data

US 2007/0185577 A1 Aug. 9, 2007

Related U.S. Application Data

(63) Continuation of application No. 10/675,573, filed on Sep. 30, 2003, now Pat. No. 7,255,714.

(51) Int. Cl.
*A61F 2/44* (2006.01)
(52) U.S. Cl. ............... 623/17.16; 623/17.11; 623/17.14
(58) Field of Classification Search .... 623/17.11–17.16
See application file for complete search history.

(56) References Cited

U.S. PATENT DOCUMENTS

| | | | |
|---|---|---|---|
| 4,401,112 A | 8/1983 | Resaian |
| 4,657,550 A | 4/1987 | Daher |
| 4,759,766 A | 7/1988 | Büettner-Janz et al. |
| 4,759,769 A | 7/1988 | Hedman et al. |
| 4,863,476 A | 9/1989 | Shepperd |
| 4,946,378 A | 8/1990 | Hirayama et al. |
| 4,946,458 A | 8/1990 | Harms et al. |
| 4,997,432 A | 3/1991 | Keller |
| 5,122,130 A | 6/1992 | Keller |
| 5,246,458 A | 9/1993 | Graham |
| 5,306,310 A | 4/1994 | Siebels |
| 5,314,477 A | 5/1994 | Marnay |
| 5,336,223 A | 8/1994 | Rogers |
| 5,401,269 A | 3/1995 | Büttner-Janz et al. |
| 5,458,641 A | 10/1995 | Ramirez Jimenez |
| 5,534,029 A | 7/1996 | Shima |
| 5,556,431 A | 9/1996 | Büttner-Janz |
| 5,562,738 A | 10/1996 | Boyd et al. |
| 5,645,596 A | 7/1997 | Kim et al. |
| 5,702,453 A * | 12/1997 | Rabbe et al. ............. 623/17.16 |
| 5,702,455 A | 12/1997 | Saggar |
| 5,713,899 A | 2/1998 | Marnay et al. |
| 5,776,198 A | 7/1998 | Rabbe et al. |
| 5,882,226 A | 3/1999 | Bell et al. |
| 5,893,889 A | 4/1999 | Harrington |
| 5,989,290 A | 11/1999 | Biedermann et al. |
| 6,019,792 A | 2/2000 | Cauthen |
| 6,063,121 A | 5/2000 | Xavier et al. |
| 6,113,637 A | 9/2000 | Gill et al. |
| 6,139,579 A | 10/2000 | Steffee et al. |
| 6,146,421 A | 11/2000 | Gordon et al. |

(Continued)

FOREIGN PATENT DOCUMENTS

DE 30 23 353 A1 4/1981

(Continued)

*Primary Examiner*—William M. Matthews
*Assistant Examiner*—Suba Ganesan
(74) *Attorney, Agent, or Firm*—Foley & Lardner LLP

(57) ABSTRACT

Intervertebral disc prostheses are provided. More particularly, the invention provides disc prostheses that have adjustable disc heights, that are readily converted into fusion prostheses and that provide a range of motions that effectively mimic the natural range of motions of a spinal disc.

7 Claims, 13 Drawing Sheets

U.S. PATENT DOCUMENTS

| | | |
|---|---|---|
| 6,179,874 B1 | 1/2001 | Cauthen |
| 6,228,118 B1 | 5/2001 | Gordon |
| 6,296,664 B1 | 10/2001 | Middleton |
| 6,368,350 B1 | 4/2002 | Erickson et al. |
| 6,375,682 B1 | 4/2002 | Fleischmann et al. |
| 6,375,683 B1 | 4/2002 | Crozet et al. |
| 6,395,034 B1 | 5/2002 | Suddaby |
| 6,454,807 B1 | 9/2002 | Jackson |
| 6,478,800 B1 | 11/2002 | Fraser et al. |
| 6,517,580 B1 | 2/2003 | Ramadan et al. |
| 6,540,785 B1 | 4/2003 | Gill et al. |
| 6,579,320 B1 | 6/2003 | Gauchet et al. |
| 6,582,466 B1 | 6/2003 | Gauchet |
| 6,582,468 B1 | 6/2003 | Gauchet |
| 6,607,558 B2 | 8/2003 | Kuras |
| 6,685,742 B1 | 2/2004 | Jackson |
| 6,730,126 B2 | 5/2004 | Boehm et al. |
| 6,764,515 B2 | 7/2004 | Ralph et al. |
| 6,966,931 B2 | 11/2005 | Huang |
| 7,022,138 B2 | 4/2006 | Mashburn |
| 7,025,787 B2 | 4/2006 | Bryan et al. |
| 7,044,970 B2 | 5/2006 | Errico et al. |
| 7,056,343 B2 | 6/2006 | Schafer et al. |
| 7,147,665 B1 * | 12/2006 | Bryan et al. .............. 623/17.16 |
| 2001/0016773 A1 | 8/2001 | Serhan et al. |
| 2001/0032020 A1 | 10/2001 | Besselink |
| 2001/0051829 A1 | 12/2001 | Middleton |
| 2002/0022888 A1 | 2/2002 | Serhan et al. |
| 2002/0107574 A1 * | 8/2002 | Boehm et al. ............ 623/17.16 |
| 2002/0111683 A1 | 8/2002 | Ralph et al. |
| 2003/0008223 A1 | 1/2003 | Fehling et al. |
| 2003/0018390 A1 | 1/2003 | Husson |
| 2003/0023312 A1 | 1/2003 | Thalgott |
| 2003/0100951 A1 | 5/2003 | Serhan et al. |
| 2003/0191534 A1 | 10/2003 | Viart et al. |
| 2004/0002762 A1 | 1/2004 | Hawkins |
| 2004/0153156 A1 | 8/2004 | Cohen et al. |
| 2004/0167626 A1 | 8/2004 | Geremakis et al. |
| 2005/0085910 A1 | 4/2005 | Sweeney |
| 2005/0165486 A1 | 7/2005 | Trieu |
| 2005/0209697 A1 | 9/2005 | Paponneau et al. |

FOREIGN PATENT DOCUMENTS

| | | |
|---|---|---|
| EP | 0 560 140 B1 | 2/1993 |
| FR | 2 805 985 | 9/2001 |
| WO | WO 95/26697 | 10/1995 |

* cited by examiner

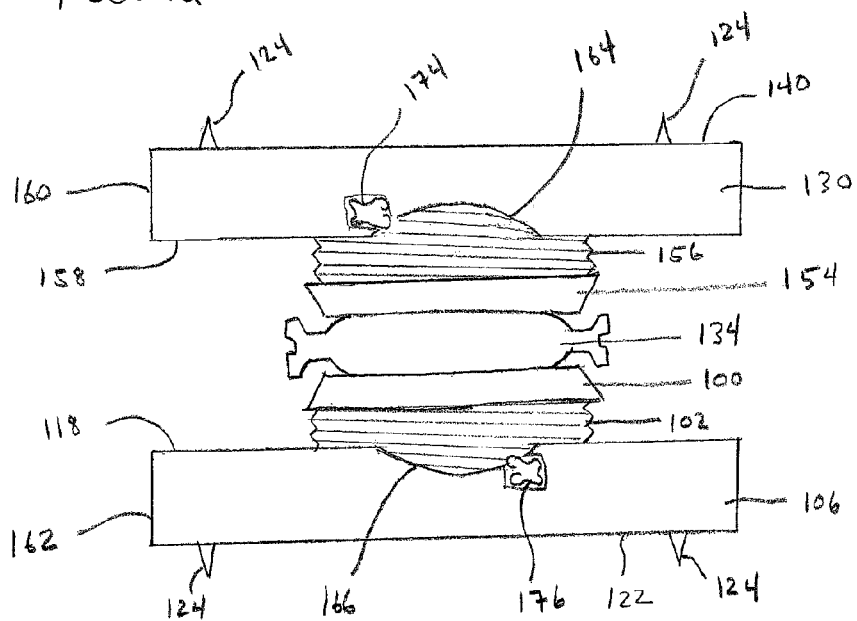
FIG. 12
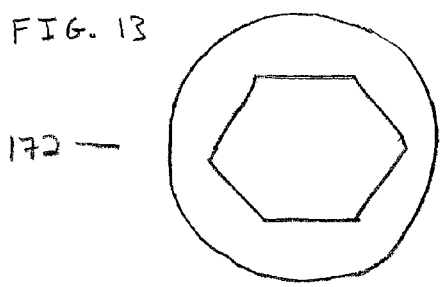
FIG. 13
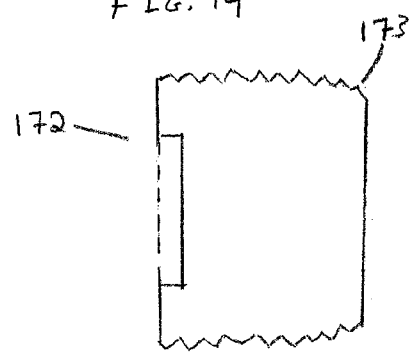
FIG. 14
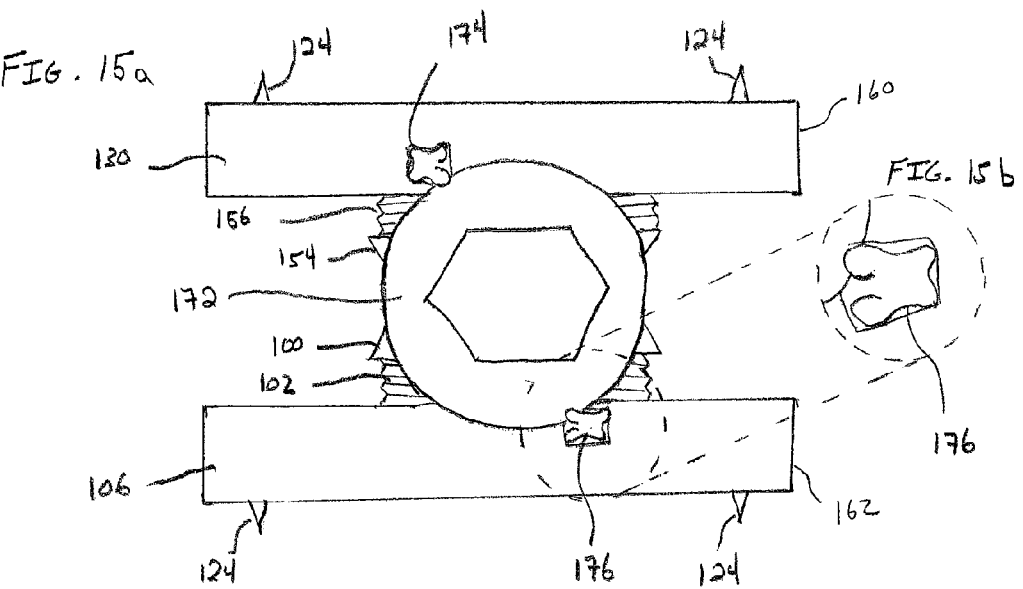
FIG. 15a
FIG. 15b

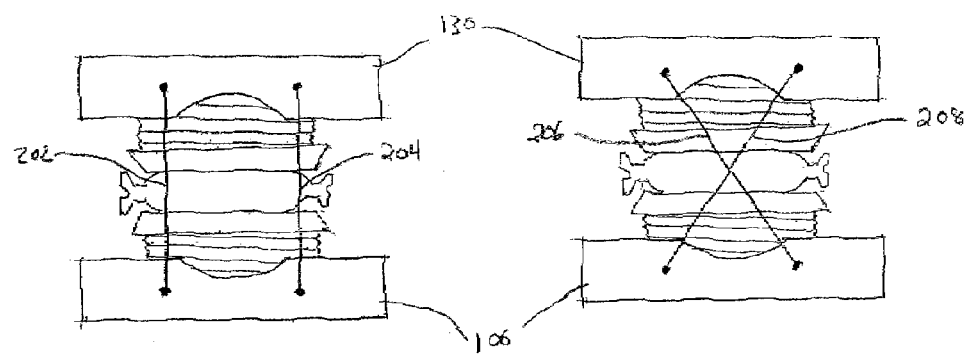
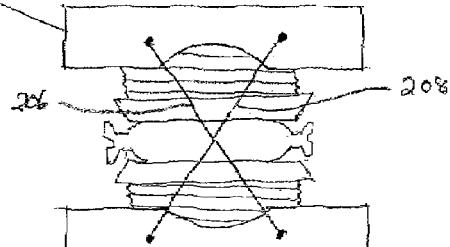
FIG. 22  FIG. 23
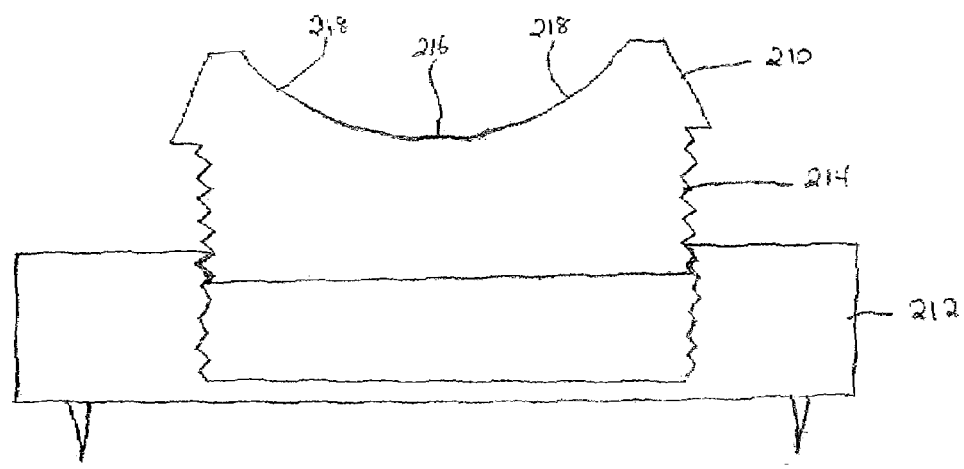
FIG. 24

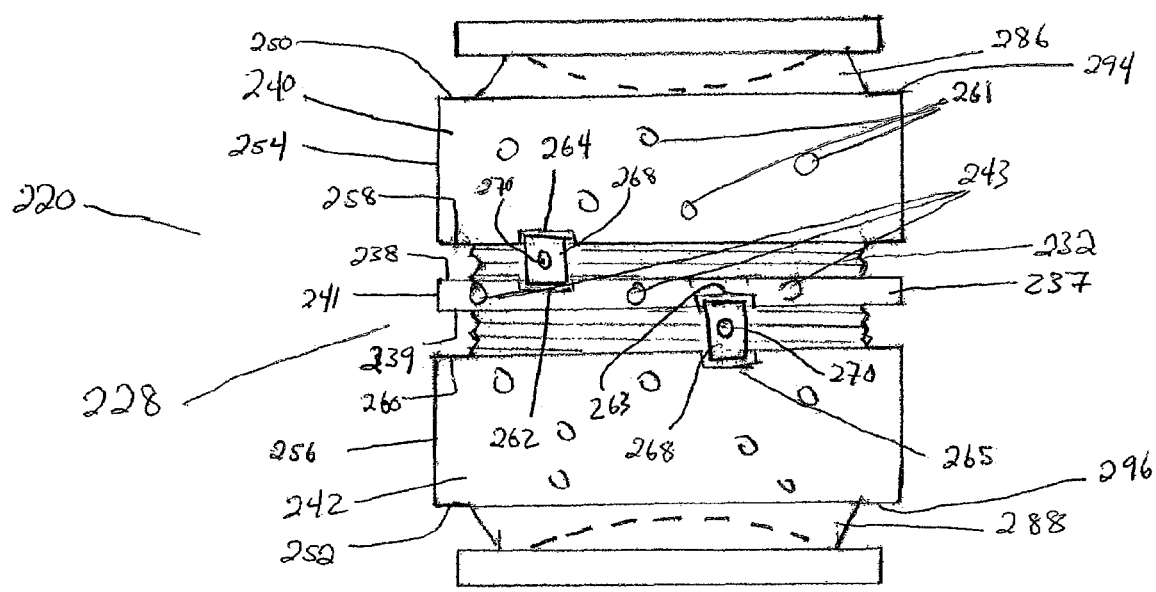

INTERVERTEBRAL DISC PROSTHESIS

CROSS-REFERENCE TO RELATED APPLICATION

This application is a continuation of and claims the benefit of U.S. patent application Ser. No. 10/675,573, filed on Sep. 30, 2003, the entire disclosure of which is incorporated herein by reference.

BACKGROUND

The present invention relates generally to the field of intervertebral disc prostheses. More particularly, the invention relates to disc prostheses that have adjustable disc heights, that are readily converted into fusion prostheses and that provide a range of motions that effectively mimic the natural range of motions of a spinal disc.

Intervertebral discs provide elastic support upon compression between adjacent vertebrae in the spine. Damage to these discs, resulting from degeneration and wear, may produce mobility limitations, pain, discomfort and even paralysis. Conventional approaches to the treatment of pathologic, degenerated or ruptured spinal discs include fusion of adjacent vertebrae and disc replacement. In a spinal fusion procedure, the faulty disc may be removed and replaced with a mechanical cage which maintains the proper disc spacing and helps support the load imposed on the spine. Ultimately, bone grows in and around the cage. The vertebrae that are involved in the fusion no longer take part in normal spinal flexing.

Disc replacement is an alternative approach to fusion. Many disc prostheses have been proposed. Unfortunately, the proposed disc prostheses suffer from practical limitations. Ideally, a disc prosthesis will mimic the range of motion of a natural vertebral disc, including side-to-side and front-to-back bending motions, compression in the axial direction and rotation and translation between vertebrae. The disc prosthesis should provide a proper disc height between vertebrae as well as proper alignment of the spine. The disc prosthesis should also be biocompatible, stable and durable. A typical disc prosthesis may be expected to last 30 years or more at approximately 2 million cycles per year.

Unfortunately, disc replacement carries significant risks. For example, distracting the vertebrae to insert or replace a disc prosthesis may injure the vertebrae, the vertebral endplates and the surrounding tissues and ligaments, including the spinal cord, nerve elements and blood vessels. This can be particularly problematic if the disc prosthesis requires repeated replacement or when it is desirable to switch from a disc prosthesis to a fusion prosthesis.

Thus, a need exists for a durable disc prosthesis that minimizes strain on the vertebrae, endplates and ligaments during insertion and replacement while providing a natural disc height and range of motion. Also desirable, is a disc prosthesis that may be easily converted into a fusion prosthesis while minimizing the risk of disc extrusion and its potentially lethal complications.

SUMMARY

Intervertebral disc prostheses are provided. In some embodiments, the disc prostheses have adjustable disc heights. In other embodiments, the disc prostheses may be readily converted into fusion prostheses. In still other embodiments, the disc prostheses provide superior axial loading capabilities. The disc prostheses may be implanted in the cervical, thoracic and lumbar regions of the spine and may be inserted via a lateral or anterior approach. The prostheses may be designed to mimic some or all of the natural degrees of motion provided by a spinal disc.

One aspect of the invention provides an intervertebral disc prosthesis having an adjustable disc height. The prosthesis includes a first base plate which has an exterior surface and an interior surface. A first cup which defines a first concave surface is disposed on the interior surface of the first base plate. The prosthesis further includes a second base plate, also having an exterior surface and an interior surface. A second cup which defines a second concave surface is disposed on the interior surface of the second base plate. The first and second base plates are disposed opposite one another in a substantially parallel relation, such the first and second cups are disposed opposite and facing one another. A disc insert having two opposing convex surfaces is disposed between and in contact with the first and second concave surfaces of the first and second base plates to provide an articulating joint. The disc prosthesis is characterized in that one or both of the first and second cups is mounted to its base plate through a vertically adjustable support.

In an alternative configuration, an intervertebral disc prosthesis having an adjustable disc height, includes a first base plate having an exterior surface, an interior surface and a cup, which defines a concave surface, disposed on its interior surface. The prosthesis further includes a second base plate having an exterior surface, an interior surface and a knob, which defines a convex surface, disposed on its interior surface. The first and second base plates are disposed opposite one another in a substantially parallel relation, such that the concave surface of the cup and the convex surface of the knob are disposed facing and in contact with one another to provide an articulating joint. The disc prosthesis is characterized in that one or both of the cup and knob is mounted to its base plate through a vertically adjustable support.

Another aspect of the invention provides a prosthesis assembly which may be readily converted from a disc prosthesis into a fusion prosthesis in situ. The prosthesis assembly includes a first base plate characterized by a circumferential edge, an interior surface and an exterior surface. A threaded groove extends into the circumferential edge along the interior surface of this first base plate. The prosthesis assembly also includes a second base plate characterized by a circumferential edge, an interior surface and an exterior surface. A threaded groove extends into the circumferential edge along the interior surface of the second base plate. The first and second base plates are disposed opposite and substantially parallel to one another, such that the grooves on their interior surfaces are disposed opposite and facing one another. A threaded rod which screws between the pair of oppositely disposed grooves on the first and second base plates is also provided. When the threaded rod is in place between the grooves, it immobilizes or partially immobilizes the two base plates. The prosthesis assembly may further include a joint disposed between the two base plates to provide one or more degrees of motion (e.g. rotating, bending, compression, translation) of a natural intervertebral disc. This joint may be removed prior to the insertion of the threaded rod to convert the assembly from a disc prosthesis into a fusion prosthesis. However, the removal of the joint is not necessary.

Still another aspect of the invention provides a disc prosthesis with improved axial loading. This disc prosthesis includes a first and a second base plate, each characterized by an exterior surface and an interior surface. A cup, which defines a concave surface, is disposed on the interior surface of each base plate and the base plates are disposed opposite and substantially parallel to each other, such that the cups are disposed opposite and facing one another. A disc insert having two opposing convex surfaces is disposed between and in contact with the first and second concave surfaces of the first and second base plates to provide an articulating joint. The disc insert is characterized in that the walls that form the two opposing convex surfaces have a plurality of compressible helical slits defined therein.

Yet another aspect of the invention provides a prosthetic vertebral assembly having a height that may be adjusted in situ. Such assemblies may be used to replace one or more vertebra and their associated intervertebral discs. In one basic embodiment the prosthetic vertebral assembly includes a prosthetic vertebral body composed of a base characterized by a superior end and an inferior end, wherein the superior end is disposed opposite the inferior end. A superior vertically adjustable support is adjustably mounted to the superior end of the base and an inferior vertically adjustable support is mounted to the inferior end of the base. A first intervertebral disc prosthesis is mounted to the superior adjustable support and a second intervertebral disc prosthesis is mounted to the inferior adjustable support, such that the base and the adjustable supports are sandwiched between the disc prostheses. In this configuration, the base and the superior and inferior adjustable supports form a prosthetic vertebra between two prosthetic discs. When the prosthetic vertebral assembly is implanted in an intervertebral space, the first and second disc prostheses are in contact with a superior and an inferior vertebra respectively. In some embodiments, the prosthetic vertebral assembly may be designed to replace more than on vertebra by linking multiple components together. For example, a prosthetic vertebral assembly may be composed of a first disc prosthesis mounted to the superior end of a first prosthetic vertebral body, a second disc prosthesis mounted between the inferior end of the first prosthetic vertebral body and the superior end of a second prosthetic vertebral body and a third disc prosthesis mounted to the inferior end of the second prosthetic vertebral body.

BRIEF DESCRIPTION OF THE DRAWINGS

FIG. 12 shows a front view of a disc prosthesis having two adjustable cups.

FIG. 13 shows a front view of a set screw that may be used to immobilize the disc prosthesis of FIG. 12.

FIG. 14 shows a cross-sectional side view of the set screw of FIG. 13.

FIG. 15a shows a front view of the disc prosthesis of FIG. 12 which has been converted into a fusion prosthesis through immobilization with the set screw of FIGS. 13 and 14.

FIG. 15b shows an enlarged view of a recoil wire that is used to prevent the set screw from becoming dislodged.

FIG. 22 shows a side view of the disc prosthesis of FIG. 12 which includes a pair of cables running substantially parallel between the base plates.

FIG. 23 shows a side view of the disc prosthesis of FIG. 12 which includes a pair of cables criss-cross between the base plates FIG. 24 shows a cross-sectional side view of a cup having a flat slit running through its concave surface. The cup is adjustably mounted to a base plate via a threaded stem.

FIG. 28 shows a front view of the prosthetic vertebral body of FIG. 27.

DETAILED DESCRIPTION

Figure 1:
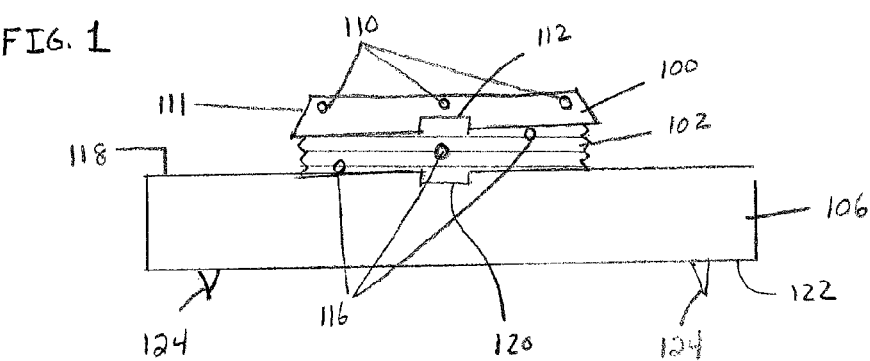
FIG. 1 shows a front view of a cup adjustably mounted to a base plate via a threaded stem.

One aspect of the invention provides intervertebral disc prostheses that do not require distraction or which minimize the degree of distraction required for their implantation. This provides an advantage over other presently known disc prostheses which require the vertebrae to be stretched further apart than their natural spacing in order to insert a prosthesis in the intervertebral space. This procedure presents an increased risk of injury to the vertebra, the vertebral endplates and the surrounding tissues and ligaments, including the spinal cord, nerve elements and blood vessels. In addition, implantation of conventional disc prostheses may require an asymmetric distraction of the vertebrae. During an asymmetric distraction the vertebrae rotate and collapse toward one another at the side opposite the distracting side. The disc prostheses provided by the present invention minimizes these risks by providing a disc prosthesis that may be inserted between two vertebrae without distraction or with minimal symmetric distraction and then expanded in situ. To the extent these prostheses distract the spine, they do so in a symmetric fashion without rotation or collapse of the vertebrae. This approach is advantageous because it minimizes facet loading.

Additionally, because the disc height of these intervertebral disc prostheses may be adjusted in situ, the prostheses may be tailored to provide a desired disc height for a particular patient. These intervertebral disc prostheses are based on an articulating joint that uses a ball-in-socket type mechanism where the joint may be expanded vertically in situ after the insertion of the prosthesis in the intervertebral space. Typically, the intervertebral disc prosthesis will include a means for simulating one or more degrees of motion of a natural intervertebral disc and a means for adjusting the disc prosthesis height in situ. The means for simulating one or more degrees of motion of a natural intervertebral disc may be a joint and the means for adjusting the disc prosthesis height in situ may be a vertically adjustable support.

In one embodiment, the disc prosthesis has an articulating joint that includes a single articulating interface defined by a concave surface and a complementary convex surface that fits into and articulates with the concave surface. For the purposes of this disclosure, a part of a disc prosthesis that defines a concave surface will be referred to as a "cup" and a part of a disc prosthesis that defines the complementary convex surface will be referred to as a "knob." At least one of the cup or the knob that define the articulating joint is mounted to a first base plate through a vertically adjustable support. The remaining knob or cup may be mounted to a second base plate through a vertically adjustable support, fixedly mounted to a second base plate or may simply be defined by a protrusion or indentation in a second base plate. For the purposes of this invention, a cup or knob is "disposed on" a base plate if it is adjustably or fixedly mounted to the base plate, or if it is defined by the surface of the base plate itself. When the disc prosthesis is in place in the intervertebral space, the first base plate and the second base plate are disposed opposite one another such that the concave and convex surfaces come together to form the articulating joint. Once the disc prosthesis is in place in the intervertebral space, the vertically adjustable support or supports may be adjusted to expand the disc height until the natural disc height is restored and the base plates are pressed more firmly against the vertebrae, stabilizing the prosthesis and minimizing the risk of disc extrusion.

In another embodiment, the disc prosthesis has an articulating joint that includes two articulating interfaces defined by two opposing cups separated by a disc insert having two oppositely disposed convex surfaces that fit into and articulate with the concave surfaces of the cups. In this design, one or both of the cups is mounted to a base plate through a vertically adjustable support. When only one cup is so mounted, the other may be fixedly mounted to a second base plate or may simply be defined by an indentation in the second base plate. When the disc prosthesis is in place in the intervertebral space, the first base plate, the second base plate and their corresponding first and second cups are disposed opposite one another with the disc insert disposed between the two cups, such that the convex surfaces of the disc insert and the concave surfaces of the cups come together to form the articulating joint. Once the disc prosthesis is in place in the intervertebral space, the vertically adjustable support or supports may be adjusted to expand the disc height until the natural disc height is restored and the base plates are forced more firmly against the superior and inferior vertebrae, stabilizing the prosthesis and minimizing the risk of disc extrusion.

The vertically adjustable support may be any support that can be adjusted in situ to change the spacing between the cup or knob mounted thereon and the base plate. As used herein, "vertically adjustable" indicates that the support may be adjusted vertically with respect to the plane of the base plate.

In one exemplary embodiment, the vertically adjustable support is composed of a threaded stem that screws into a complimentarily tapped bore in a base plate. The bore may extend into or through the base plate. Using this construction, the disc height of the prosthesis may be increased or decreased by rotating the stem within the bore in one direction or the other. The adjustable support and/or threaded stem may optionally include a stop which prevents the disc height from changing once the support has been adjusted.

In one variation on the above-described embodiment, the vertically adjustable support is a stem onto which a cup or knob is mounted. An axial tapped bore extends into the stem that screws onto a threaded stem extending from the base plate. Using this construction, the disc height of the prosthesis may be increased or decreased by rotating the tapped bore on the threaded stem in one direction or the other. The adjustable support may optionally include a stop which prevents the disc height from changing once the support has been adjusted.

In another design, the adjustable support may be a stem having a saw-tooth-like pattern along its edge. In this design, the ratcheting teeth along the stem engage with reciprocating teeth in a bore in the base plate allowing the cup or knob mounted to the adjustable support to be jacked up from the base plate in a step-wise fashion. Yet another design combines a screw-type rotational motion and a ratcheting mechanism. In this embodiment a threaded stem screws out of a tapped bore in the base plate and at regular intervals ratchets along the stem engage reciprocating teach in the bore to prevent unintended retraction.

Other suitable vertically adjustable supports include, but are not limited to, those based on a cam mechanism, such as that described in U.S. Pat. No. 4,863,476 and those based on an expandable/collapsible bellows, such as that described in U.S. Pat. No. 6,375,682.

The adjustable support and the cup or knob mounted thereon are desirably, but not necessarily, removably attached to the underlying base plate such that they may be completely detached from the disc prosthesis. This allows the cup or knob to be replaced when an articulating joint begins to wear out or fails. Alternatively, the removal of the articulating joint allows the disc prosthesis to be converted into a fusion prosthesis. This may be accomplished by inserting a cage between the base plates to immobilize the base plates between the vertebrae. In the embodiments provided above, the adjustable support could be removed from its base plate simply by unscrewing the threaded stem from its tapped bore or by ratcheting the saw-toothed stem out of its bore.

The base plates to which the adjustable supports are anchored may be designed to provide multiple sites of attachment for the adjustable supports. For example, a base plate may include more than one bore along its anterior-posterior axis for receiving a threaded stem. By changing the location of the adjustable supports on the base plates, the placement of the articulating joint and its center of articulation may be tailored to meet the specific needs of a given patient.

The base plates may be made of any suitable biocompatible material and may optionally be made of or coated with a porous material to allow bone and/or tissue growth therethrough. Alternatively, the base plates may be made of a fenestrated biocompatible material that allows bone and/or tissue growth therethrough. Suitable biocompatible materials include, but are not limited to, metals such as titanium, titanium alloys, chrome cobalt, or stainless steel. Other biocompatible materials include, but are not limited to, graphite and ceramics, such as hydroxapatites. Plastics may also be employed. Suitable plastics include, but are not limited to, polyethylene (e.g. ultra high molecular weight polyethylene) and polyether ester ketone.

The exterior surfaces of the base plates (i.e., the surfaces that are adapted to be attached to the superior and inferior vertebrae defining the intervertebral space) may be flat, but are desirably convex, such that they match the natural contours of the vertebral endplates. The exterior surfaces and interior surfaces (i.e. the surfaces that face the intervertebral space when the disc prosthesis is in place) of the base plates may be substantially parallel or may define a small angle (e.g., less than about 10 degrees), providing a wedge shaped plate. The circumferential shape of the base plates is not critical, but should be chosen to provide a stable foundation for the disc prosthesis against the vertebral endplates. As such, the base plates desirably cover the endplates of the vertebrae substantially completely in order to avoid the application of pressure to and the puncturing of the softer tissue in the nucleus of the endplates. In some instances the base plates may have a oval circumference. In other instances the base plates may have a kidney-like circumference that mimics the natural circumferential shape of the vertebrae. The base plates may be anchored to the vertebral endplates through any suitable attachment means, many of which are well known. For example, the base plates may be fastened to their respective endplates through bone screws, pins, pegs, teeth and the like.

The circumferential shape of the concave or convex surfaces that are defined by the knobs or cups may take on a variety of shapes, including circular or ellipsoidal. An ellipsoidal shape is advantageous because such a shape limits axial rotation without constraining flexion and extension or lateral bending in the direction parallel to the short axis of the ellipsoid. When the concave surfaces have an ellipsoidal circumferential shape, the long axis of the ellipsoid may run parallel to the anterior-posterior axis of the base plate, perpendicular to the anterior-posterior axis of the base plate, or at an angle between parallel and perpendicular.

In some embodiments, the concave surfaces will include a flat strip dividing the apex of the concavity. When this concave surface engages a complimentary convex surface, the strip allows for translation of the convex surface along the flat strip of the concave surface, as well as rotation. By providing for translation, excessive stresses on the disc prosthesis may be alleviated. The flat strip preferably runs along the concave surface in a direction that is substantially perpendicular to the anterior-posterior axis of the prosthesis, however other orientations are possible.

The cups and/or knob may be positioned on the base plates such that the vertical axes through the centers of their concave or convex surfaces coincide with the midpoint of the anterior-posterior axes of the base plates. Alternatively, the vertical axes through the centers of the concave or convex surfaces may be displaced posteriorly with respect to the midpoints of the anterior-posterior axes of the base plates. The latter embodiment may be advantageous because it more accurately reproduces the natural center of articulation of the spine.

Like the base plates, the disc inserts may be made of any suitable biocompatible material, including those listed above. In some embodiments, the disc insert is desirably made from a plastic, such as polyethylene. The circumferential shape of the oppositely disposed convex surfaces will reflect the circumferential shape of the concave surfaces. Thus, in some embodiments the circumferential shape of the convex surfaces will be circular or ellipsoidal. The opposing surfaces are desirably, but not necessarily, bilaterally symmetric. A radioopaque marker may optionally be incorporated into the disc insert to facilitate x-ray detection of the insert. For example, the disc insert may have a ring made from a radioopaque material disposed in a groove around the circumference of the insert. Alternatively, the disc insert may have a plate made from a radioopaque material disposed laterally through its central portion.

In order to provide for axial loading of the disc prosthesis, the disc insert may optionally be a compressible insert. For example, the disc insert may define one or more compressible slits around at least a portion of the periphery of its external surface in order to provide for axial loading. The disc insert may optionally include a central collar separating the two oppositely disposed convex surfaces. The collar may include a flat ring around the periphery of the disc insert, which allows for translation between the convex and concave surfaces, and an outer circumferential wall.

A second aspect of the invention provides an intervertebral prosthesis assembly that may be readily converted from a disc prosthesis into a fusion prosthesis. These assemblies make it possible for a physician to change the approach for treating back pain and disc degeneration from a reconstruction or replacement of the degenerated joint to a spinal fixation and fusion using a single assembly. The assemblies are converted from a disc prosthesis into a fusion through the immobilization of the disc prosthesis in situ and may be used in the event of a disc failure.

The basic features of the assembly include two base plates, each adapted to be fixed to one of two vertebrae that define an intervertebral space. The base plates each have an circumferential edge, an exterior surface and an interior surface. When the prosthesis is inserted into the intervertebral space, the two base plates are disposed opposite one another. In this configuration, one base plate is fastened to the superior vertebral endplate and is referred to as the superior base plate. The other base plate is fastened to the inferior vertebral endplate and is referred to as the inferior base plate. The superior base plate has at least one threaded groove extending into its circumferential edge along its interior surface. Similarly, the inferior base plate has at least one threaded groove extending into its circumferential edge along its interior surface. The grooves on the opposing plates are positioned such that they are disposed opposite and facing one another when the prosthesis is in place in the intervertebral space. In order to ensure that the base plates have the correct alignment when they are inserted, they may include some sort of marking (e.g. a line etched in the circumferential edges) that lines up when the base plates are correctly positioned. The threads in the grooves are adapted to engage with a threaded rod such that the rod may be screwed into place between the grooves to prevent the prosthesis from articulating. In this configuration, the rod serves as a cage in the fusion prosthesis. It is advantageous to provide as large a cage as possible in the fusion prosthesis, therefore, it is desirable for the threaded groove and the cage (i.e. threaded rod) to extend into the prosthesis assembly as far as possible. For example, if the prosthesis assembly includes a ball-in-socket type joint, the groove may extend to the cups and/or knobs that form the joint.

The two base plates may include a single pair of oppositely disposed grooves or may include two or more pairs of oppositely disposed grooves located at different positions along their circumferential edges. For example, the circumference of the base plates may be characterized as having a ventral edge (i.e. a portion of the circumferential edge that faces anteriorly when the prosthesis is in place in an intervertebral space), a dorsal edge (i.e. a portion of the circumferential edge that faces posteriorly when the prosthesis is in place in an intervertebral space) and a first and second lateral edge (i.e. portions of the circumferential edge that face laterally when the prosthesis is in place in an intervertebral space). In some embodiments, the base plates will define a single pair of opposing threaded grooves located along the ventral or lateral edges of the base plates. In other embodiments, the base plates will each define two or more pairs of opposing threaded grooves located along their ventral or lateral edges. In still other embodiments, multiple pairs of opposing threaded grooves may be located along a single portion of the circumferential edge (e.g. ventral or lateral). It should be understood that the different portions (ventral, dorsal and lateral) of the circumferential edge of a base plate may not be rigidly defined, depending upon the shape of the base plate. However, the term "ventral edge" may generally encompass any portion of the circumferential edge that is accessible from an anterior approach, the term "lateral edge" may generally encompass any portion of the circumferential edge that is accessible from a lateral approach and the term "dorsal edge" may generally encompass any portion of the circumferential edge that is accessible from a posterior approach.

The rod desirably has an outside diameter that is large enough to distract the vertebrae sufficiently to press the base plates snugly against the vertebrae, stabilizing the fusion prosthesis and preventing the base plates from separating further during use. Again, it should be noted that the term "rod" as used herein is not intended to denote only a solid cylinder. The cylinder may be hollow. The threaded rod desirably has a tapered leading edge. This is advantageous because it allows the threaded rod to be introduced into the cavity defined by the opposing grooves without first having to distract the vertebrae. In this configuration, the threaded rod passes into the cavity until it engages the threads in the opposing grooves. Once the threads have been engaged, the rod may be screwed between the grooves, causing the superior and inferior base plates to distract.

The base plates and the threaded rod may be made of any suitable biocompatible material and are desirably made of or coated with a porous material or of a fenestrated biocompatible material which allows bone and/or tissue growth therethrough.

When the prosthesis assembly is acting as a disc prosthesis, it will include a joint sandwiched between the two base plates. The joint may be any mechanism that simulates one or more of the natural degrees of motion of the spinal column. Various types of joints for providing degrees of motion are known. These include ball-in-socket mechanisms made from complementary concave and convex surfaces that form an articulating joint between two opposing base plates. Other disc prosthesis include a flexible rubber or polymeric insert disposed between two base plates to replicate natural spinal motion. Still other disc prosthesis include mechanical damping mechanisms, such as springs, disposed between opposing base plates in order to mimic natural spinal motion. Any of these joints which replicate one or more degrees of spinal motion may be utilized in the prosthesis assemblies provided herein. In some embodiments the means for providing motion, such as an articulating ball-in-socket type joint, is offset posteriorly with respect to the anterior-posterior axes of the base plates. This design more accurately simulates the position of the natural center of articulation and provides more space for and easier access to a pair of opposing threaded grooves along the ventral edge of the base plates.

The joint is desirably, but not necessarily, removable, such that it may be removed prior to the insertion of the threaded rod which converts the disc prosthesis into a fusion prosthesis. For example, when a disc prosthesis having an articulating joint composed of a disc insert disposed between two cups, as described in detail above, is used, the disc insert and the cups may be removed prior to immobilizing the base plates. Alternatively, the insert could be immobilized by rigidly attaching it to the prosthesis assembly. In one such configuration, the disc insert may include a tapped bore into which a screw may be inserted to fasten the insert to the threaded rod.

The range of rotational motion provided by the disc prostheses may optionally be restricted in order to provide more natural disc-like movement. This may be accomplished by securing one or more cables between the superior and inferior base plates such that the cables prevent unrestricted rotation of one plate with respect to the other. One or more cables may be used and they may be attached to the base plates at a variety of locations. The cables are preferably attached to the circumferential edge of the base plates. When multiple cables are used, neighboring cables may be attached between the base plates in a substantially parallel relation or they may be attached such that they criss-cross. The cables may be attached to the base plates by any suitable means, such as with welds, hooks, pins, snaps, and the like. The cables may be rigidly or removably fixed to the base plates. The latter embodiment is advantageous because it allows the cables to be moved out of the way in order to make adjustments to the prosthesis. The cables may be made of any biocompatible material that is sufficiently elastic to provide a limited degree of rotational motion. In one embodiment, the cables are made from a memory metal alloy that exhibits super-elastic properties at body temperature. A discussion of suitable biocompatible memory metal alloys may be found in U.S. Patent Application Publication No. 2003/0009223, which is incorporated herein by reference. Stainless steel is another example of a suitable materials from which the cables may be made.

Another aspect of the invention provides a prosthetic vertebral assembly that may be used to replace one or more vertebrae and the intervertebral discs associated therewith. The height of the assemblies may be vertically adjusted, that is adjusted in the direction along the long axis of the spinal column when the assemblies are implanted. This feature makes it easy to tailor the assembly height to a particular patient and to adjust the height of in situ if necessary. The assemblies include at least one vertically adjustable prosthetic vertebral body that is made from a base having a superior end and an inferior end, where the term "superior end" refers to the end of the body that faces a superior vertebra when the assembly is implanted in a spine and the term "inferior end" refers to the end of the body that faces an inferior vertebra when the assembly is implanted in a spine. A superior vertically adjustable support is adjustably mounted to the superior end of the base and an inferior vertically adjustable support is adjustably mounted to the inferior end of the base. A first intervertebral disc prosthesis is attached to the superior vertically adjustable support and a second intervertebral disc prosthesis is attached to the inferior vertically adjustable support, such that the prosthetic vertebral body is sandwiched between the first and second disc prosthesis in a generally axial alignment. The prosthetic vertebral body may optionally be adapted to accept screws, or other attachments means, that would permit the prosthetic vertebral body to accept a stabilizing device for stabilizing the prosthetic vertebral assembly in a patient's spine.

The vertically adjustable supports may be any supports that may be adjusted in situ to change the overall height of the prosthetic vertebral body. In one exemplary embodiment, the base of the prosthetic vertebral body comprises a threaded rod characterized by a superior end and an inferior end and the first and second vertically adjustable supports each define a tapped bore, extending into one surface thereof, which screws onto one end of the threaded rod. In this design the height of the prosthetic vertebral body may be increased or decreased by rotating one or both of the supports on the threaded rod in one direction or the other. The adjustable supports and/or the threaded rod may optionally include a stop which prevents undesired expansion or contraction of the prosthetic body height once it has been properly adjusted.

In another embodiment, the base of the prosthetic vertebral body defines a tapped bore extending through the base, or two oppositely disposed tapped bores extending into opposing sides of the base, and the superior and inferior vertically adjustable supports are threaded rods adapted to screw into opposite ends of the tapped bore or into oppositely disposed tapped bores in the prosthetic vertebral body. Using this construction, the height of the prosthetic vertebral body may be increased or decreased by rotating the threaded rods in the tapped bore or bores in one direction or the other. The adjustable supports and/or the tapped bore(s) may optionally include a stop which prevents undesired expansion or contraction of the prosthetic body height once it has been properly adjusted.

Alternatively, the base of the prosthetic vertebral body may comprise a stem having a saw-tooth-like pattern along its periphery at one end and an opposing saw-tooth like pattern along its periphery at the opposing end. In this design, the ratcheting teeth along one end of the stem engage with reciprocating teeth in a bore defined by the superior support and the ratcheting teeth along the opposing end of the stem engage with reciprocating teeth in a bore defined by the inferior support, such that the height of the prosthetic vertebral body may be increased by jacking up one or both supports on the stem. Yet another design combines a screw-type rotational motion and a ratcheting mechanism. In this embodiment the base of the prosthetic vertebral body is a threaded stem having ratchets at regular intervals that engage reciprocating teeth in the tapped bores of the adjustable supports to prevent unintended contraction of the prosthetic body height.

The base and the superior and inferior vertically adjustable supports may be made of any suitable biocompatible material. Suitable biocompatible materials include, but are not limited to, metals such as titanium, titanium alloys, chrome cobalt, or stainless steel. Other biocompatible materials include, but are not limited to, graphite and ceramics, such as hydroxapatites. Plastics may also be employed. Suitable plastics include, but are not limited to, polyethylene (e.g. ultra high molecular weight polyethylene) and polyether ester ketone.

The dimensions (e.g. lateral and anterior-posterior widths) of the prosthetic vertebral body are desirably designed to mimic those of a natural vertebra. The prosthetic vertebral body, and the superior and inferior vertically adjustable supports in particular, may have a variety of circumferential shapes, however, the circumferential shape preferably will be generally cylindrical.

The first and second intervertebral disc prostheses that are mounted to opposing ends of the prosthetic vertebral body may have a variety of designs, provided they are adapted to be mounted to the vertebral body in a configuration and alignment that allows them to replace a natural intervertebral disc when the prosthetic vertebral assembly is implanted into a patient's spine. The disc prostheses may be mounted to the prosthetic vertebral body by any suitable means, including but not limited to, screws, pins, welds, and the like. In some embodiments the disc prostheses may be mounted to the prosthetic body by allowing one or both of the vertically adjustable supports serve as a part of the disc prostheses.

Typically, a suitable intervertebral disc prosthesis will include a joint sandwiched between a superior base plate and an inferior base plate. The joint may by any mechanism that simulates one or more of the natural degrees of motion of a spinal column. Examples of suitable joints include, but are not limited to, those based on a ball-in-socket type interface, those based on a flexible rubber or polymeric insert and those based on a mechanical damping mechanism, such as a spring. In some embodiments, the superior and/or inferior vertically adjustable supports will themselves provide base plates for the disc prostheses.

One or both of the intervertebral disc prostheses of the prosthetic vertebral assembly may be an intervertebral disc prosthesis having an adjustable disc height. Such vertically adjustable disc prostheses are discussed in detail above. The combination of a prosthetic vertebral body having a vertically adjustable body height with one or more disc prostheses having vertically adjustable disc heights is advantageous because it provides the surgeon with a great deal of flexibility in tailoring the prosthetic vertebral assembly for a given patient.

In some instances several intervertebral disc prostheses may be combined with two or more prosthetic vertebral bodies in order to replace entire portions of a patient's spine. For example, an assembly could be composed of a first prosthetic vertebral body sandwiched between a first and a second intervertebral disc prosthesis and a second vertebral body sandwiched between the second and a third intervertebral disc prosthesis.

The disc prostheses and prosthetic assemblies provided herein may be further illustrated by the non-limiting embodiments discussed below in connection with the figures. However, these embodiments are intended only to exemplify the invention and should not be construed to limit the invention to any particular embodiment. The drawings are not necessarily to scale and the relative dimensions of the disc prostheses and prosthesis assemblies provided therein may deviate from those shown in the figures.

Figure 2:
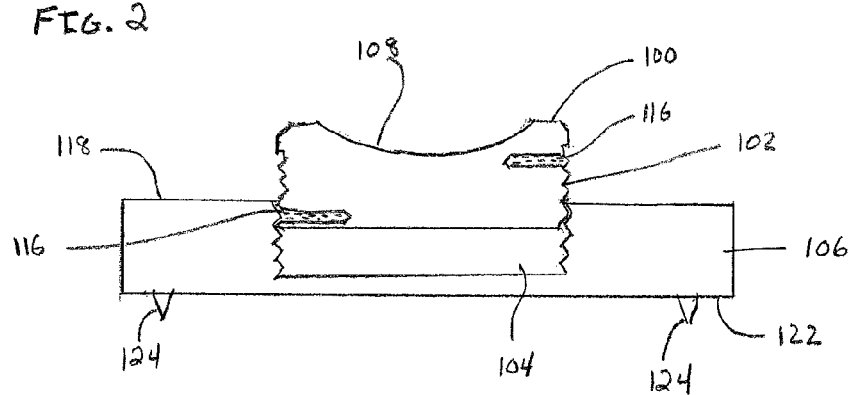
FIG. 2 shows a cross-sectional front view of the cup/stem/base plate assembly of FIG. 1.
Figure 3:
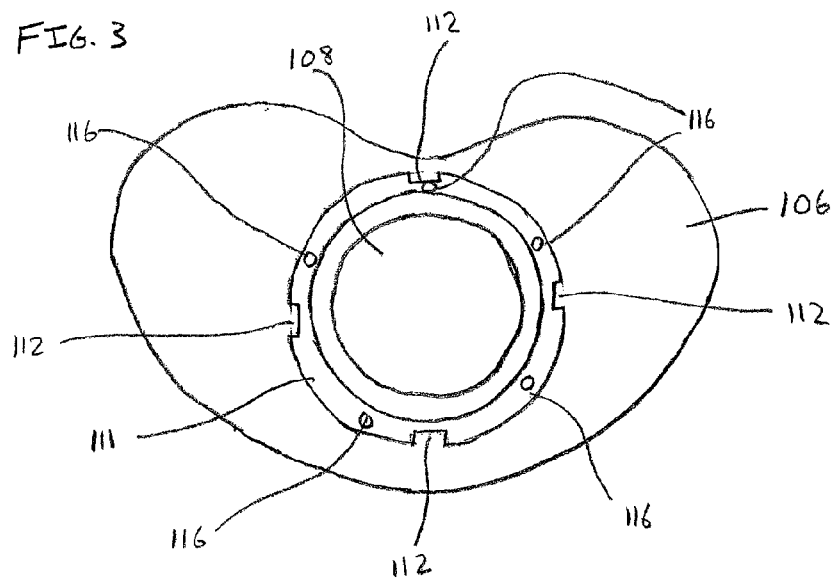
FIG. 3 shows a top view of the cup/stem/base plate assembly of FIG. 1.

FIG. 1 shows a front view of an assembly including a cup adjustably mounted to a base plate in accordance with one embodiment of the present invention. FIG. 2 shows a cross-sectional view of the assembly of FIG. 1 and FIG. 3 shows a top view of the assembly of FIG. 1. The assembly includes a cup 100 mounted on a threaded stem 102 which screws into a tapped bore 104 in a base plate 106. The cup defines a concave surface 108 and has a plurality of holes 110 disposed around its circumferential edge 111. These holes are adapted to engage with a tool that may be used to rotate the cup in situ. In FIG. 1, the cup further includes four equi-spaced notches 112 cut into the periphery of its circumferential edge, however, a different number of notches and different notch placements are possible. A plurality of tapped holes 116 extend radially into the threaded stem. As the threaded stem is rotated from its lowest position upward, the tapped holes in the stem become exposed above the interior surface 118 of the base plate 106. The tapped holes are vertically displaced from one another around the circumference of the threaded stem, such that more tapped holes become exposed as the threaded stem is rotated upward. For example, the tapped holes may be displaced such that one additional tapped hole becomes exposed every time the threaded stem is raised an additional 1 millimeter in height. However, other displacements are also possible. The base plate includes at least one notch 120 that may be disposed opposite and facing a notch on the circumferential edge of the cup. The external surface 122 of the base plate includes a plurality of pins 124 adapted to attached the base plate to the endplate of a vertebra.

Figure 4:
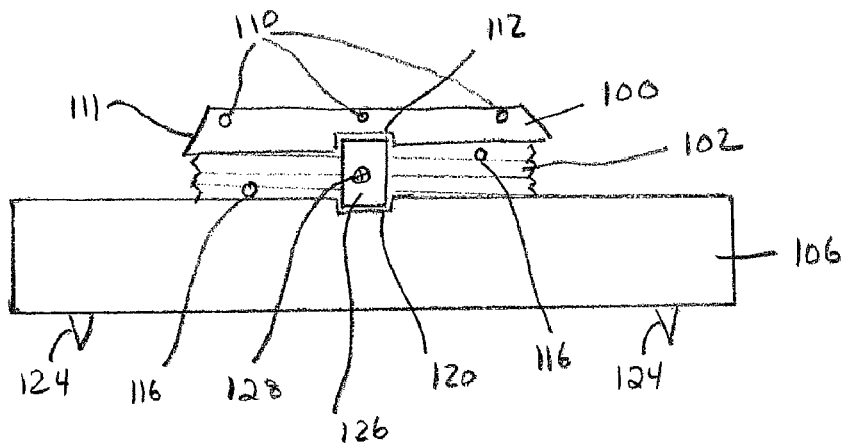
FIG. 4 shows a front view of the cup/stem/base plate assembly of FIG. 1, including a tab which locks in the height of the cup relative to the base plate.
Figure 5:
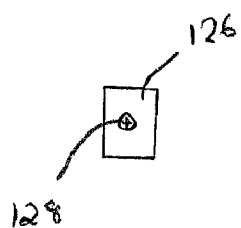
FIG. 5 shows a front view of the tab of FIG. 4.
Figure 6:
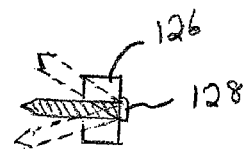
FIG. 6 shows a cross-sectional side view of the tab of FIG. 4.
Figure 7:
FIG. 7 shows a top view of the tab of FIG. 4.
Figure 8:
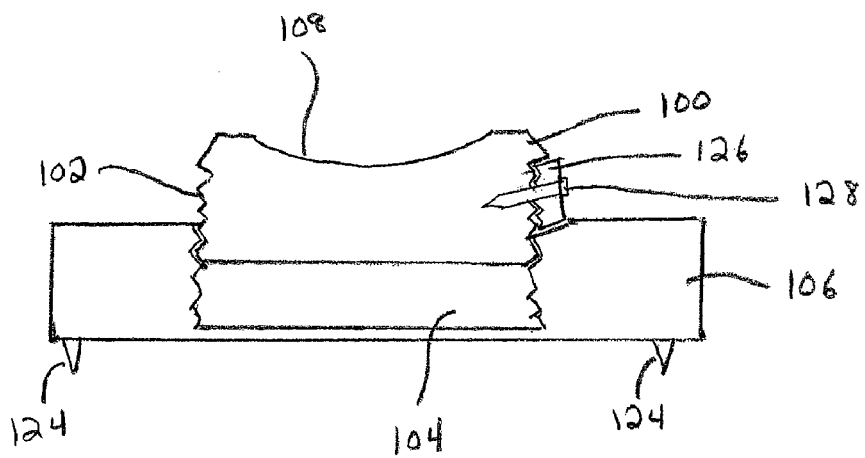
FIG. 8 shows a cross-sectional side view of the cup/stem/base plate assembly of FIG. 4.

FIG. 4 shows how the notches on the cup and the base plate may be used to lock in the height of the cup above the base plate. When the notch 120 on the base plate 106 is lined up opposite a notch 112 on the circumferential edge 111 of the cup 100, the two notches form a frame into which a tab 126 may be fastened against the threaded stem 102 using a screw 128 that engages one of the tapped holes 116 extending radially into the stem. When the tab is in place the threaded stem is unable to rotate. FIGS. 5-7 show a exemplary tab that may be used to lock in the height of the cup in FIG. 4. FIG. 5 is a front view of the tab 126 and includes a front view of a screw 128 extending through the tab and adapted to fit a tapped hole 116 in the threaded stem 102. FIG. 6 shows a cross-sectional side view of the tab and screw. As shown in figure, the screw may be aligned at a substantially right angle with respect to the long axis of the tab (solid line), or may be aligned at a different angle (dotted lines) to make it more accessible in situ. FIG. 7 shows a top view of the tab and screw. Here the contour of the inner surface of the tab matches the contour of the outer surface of the threaded rod to provide a snug fit when the tab is screwed into place. Although the tab and the frame in FIG. 4 are generally rectangular in shape, it should be understood that a variety of alternative shapes may also be employed. FIG. 8 shows a cross-sectional side view of the tab of FIGS. 5-7 inserted into the assembly of FIG. 1. As illustrated in FIG. 8, when the tab is screwed in at an angle, the notches on the cup and the base plate that form the frame, should also be cut at an angle.

It is also possible to lock the cup against the base plate when the cup is in its fully contracted position. This may be accomplished by fastening an appropriately sized tab into the frame formed by two opposing notches when the cup is resting against the base plate. In one embodiment, the tab is fastened into place by screwing it directly to the base plate itself. In this embodiment, the tab includes a screw aperture through which a screw may be inserted. The screw may then be screwed into a tapped hole in the base plate, fixing the tab in the frame.

It should be noted that although the assembly of FIGS. 1-4 and 8 refer to a disc prosthesis where a cup is mounted to a vertically adjustable support, an analogous design could also be used where a knob is mounted to a vertically adjustable support.

Figure 9:
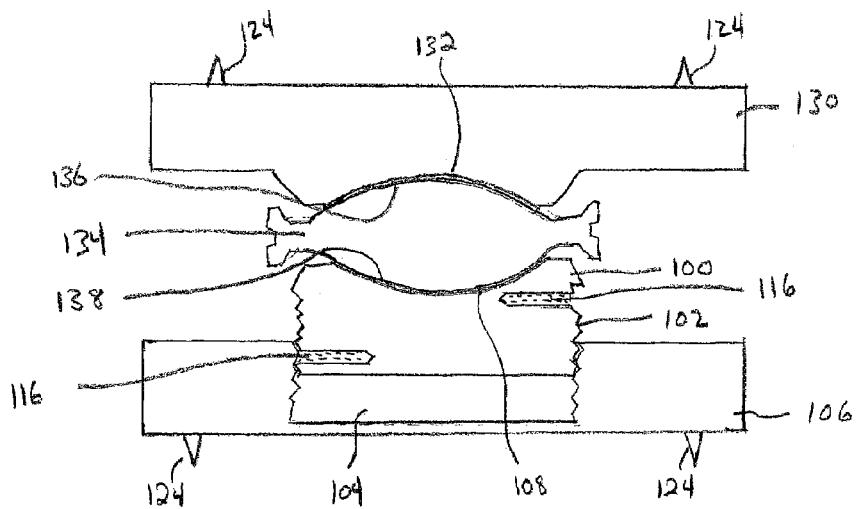
FIG. 9 shows a cross-sectional front view of a disc prosthesis, including the cup/stem/base plate assembly of FIGS. 1-4.

A cross-sectional front view of one exemplary disc prosthesis that includes the assembly of FIG. 1 is shown in FIG. 9. The disc prosthesis includes a superior base plate 130 defining a first concave surface 132, a disc insert 134 having two oppositely disposed convex surfaces 136, 138, and the inferior base plate 106 and cup 100 which provides a second concave surface 108. As discussed above, the cup is mounted on a threaded stem 102 which screws into a tapped bore 104 in the inferior base plate to provide a vertically adjustable support. The external surfaces 140, 122 of the superior and inferior base plates include pins 124 to anchor the base plates to vertebral endplates.

Figure 10:
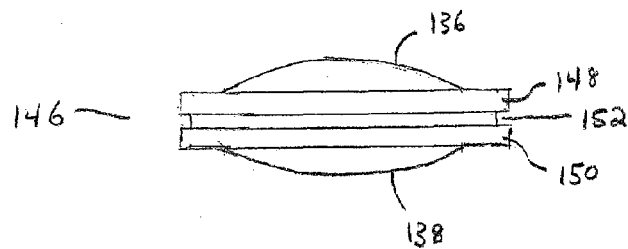
FIG. 10 shows a front view of a disc insert for a disc prosthesis.

FIG. 10 shows a front view of the disc insert of the disc prosthesis of FIG. 9. As shown in the figure, the insert includes a collar 146 around its midsection. This collar has an upper rim 148 and a lower rim 150 separated by a circumferential groove 152 which is adapted to receive a radioopaque ring (not shown) in order to locate the disc prosthesis in situ via x-ray imaging.

Figure 11:
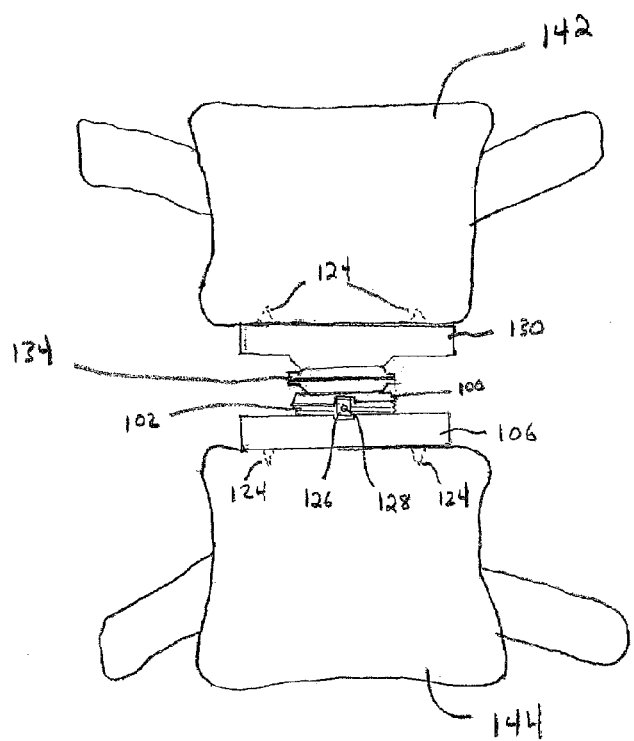
FIG. 11 shows a front view of the disc prosthesis of FIG. 9 in place between two vertebrae.

FIG. 11 shows the disc prosthesis of FIG. 9 inserted into the intervertebral space between a superior vertebra 142 and an inferior vertebra 144. In the figure, the tab 128 that locks in the height of the cup 100 relative to the inferior base plate 106 faces in an anterior direction which makes it more easily accessible in situ.

A prosthesis assembly that may be converted from a disc prosthesis into a fusion prosthesis is presented in FIG. 12. This assembly is based on an articulating joint of the type shown in FIG. 9. Unlike the disc prosthesis of FIG. 9, however, both cups 100, 154 of prosthesis of FIG. 12 are vertically adjustably mounted to their respective base plates 106, 130 on threaded stems 102, 156. The superior base plate 130 has an exterior surface 140 adapted to be attached to a vertebral endplate through a plurality of pins 124, an interior surface 158 that faces into the intervertebral space when the disc prosthesis is in place and a circumferential edge 160. Similarly, the inferior base plate 106 has an exterior surface 122 adapted to be attached to a vertebral endplate through a plurality of pins 124, an interior surface 118 that faces into the intervertebral space when the disc prosthesis is in place and a circumferential edge 162. A first threaded groove 164 extends into the circumferential edge of the superior base plate along its interior surface and a second threaded groove 166 extends into the circumferential edge of the inferior base plate along its interior surface.

Figure 16:
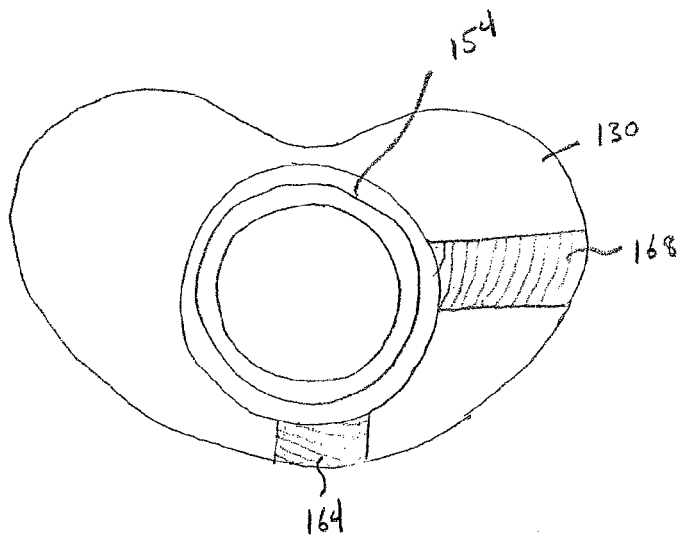
FIG. 16 shows a bottom view of the superior cup/stem/base plate assembly of the disc prosthesis of FIG. 12.
Figure 17:
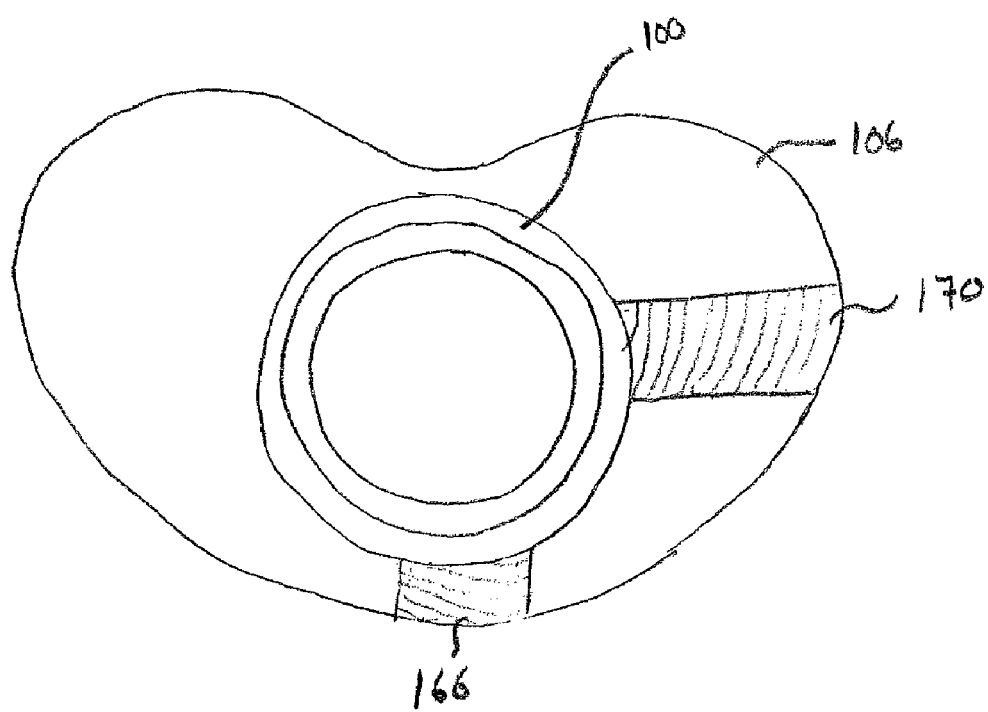
FIG. 17 shows a top view of the inferior cup/stem/base plate assembly of the disc prosthesis of FIG. 12.

The threading in the grooves is best seen in FIGS. 16 and 17. FIG. 16 shows the view looking up at the superior base plate 130. FIG. 17 shows the view looking down on the inferior base plate 106. In the embodiment depicted in FIGS. 16 and 17, both base plates include two threaded grooves, one at the ventral edge 164, 166 and one at the lateral edge 168, 170.

It should be noted that the vertically adjustable cups shown in FIG. 12 could also include the notch/tab configuration of FIG. 4 in order to lock in the height of the cups relative to the base plates, although such a configuration is not explicitly shown in FIG. 12.

Figure 15C:
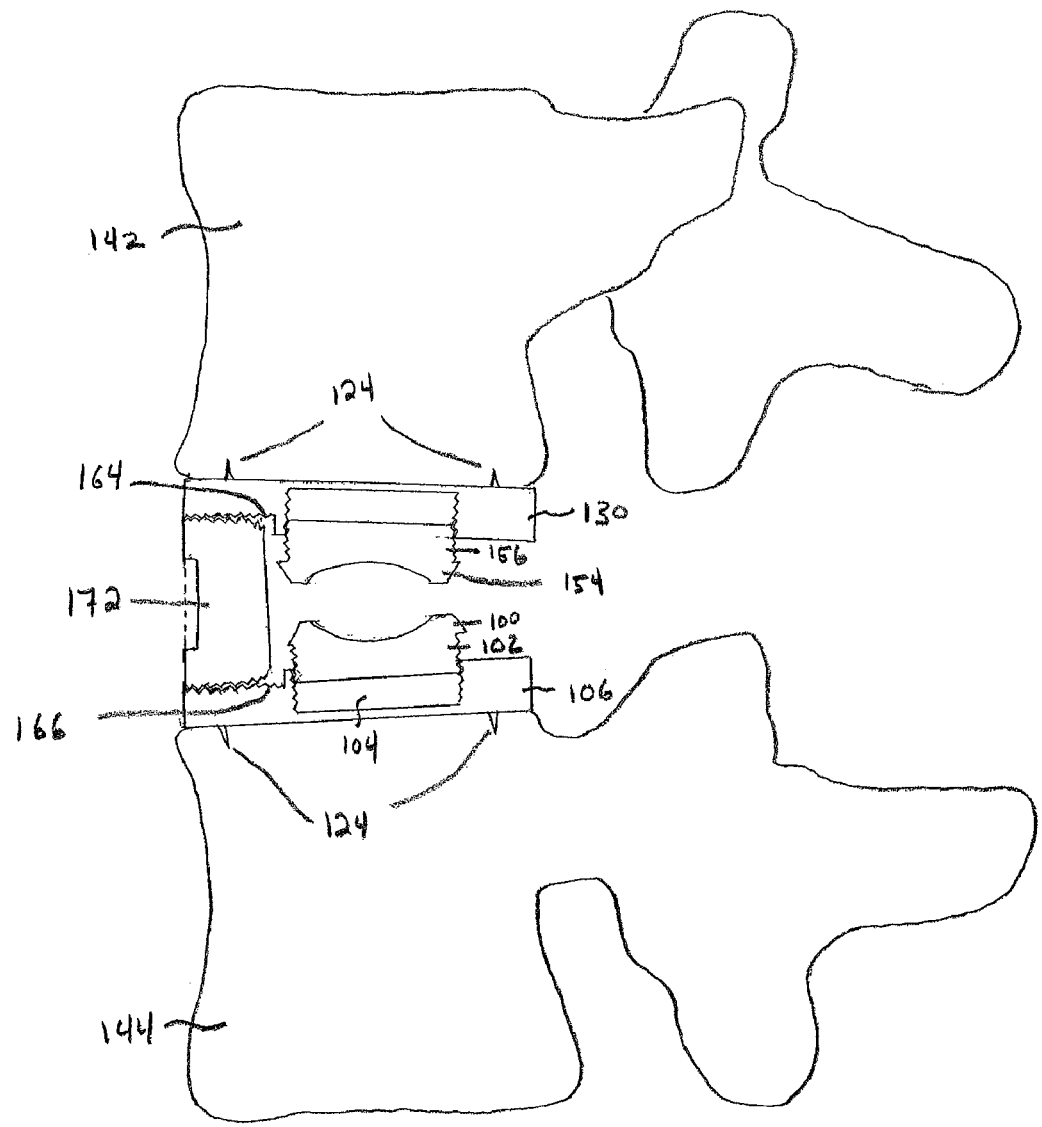
FIG. 15c shows a cross-sectional side view of the fusion prosthesis of FIG. 15a implanted between two vertebrae.

In order to convert the prosthesis assembly of FIG. 12 into a fusion prosthesis, the base plates may be immobilized by screwing a threaded rod, such as a set screw 172, between opposing grooves in the superior and inferior base plates. FIGS. 13 and 14 depict a front and cross-sectional side view, respectively, of a suitable set screw having a tapered leading edge 173. FIGS. 15a and c show a front view and a cross-sectional side view, respectively, of the prosthesis assembly of FIG. 12. In FIG. 15c the prosthesis assembly is implanted between a superior vertebra 142 and an inferior vertebra 144. The prosthesis assembly shown in FIGS. 15a and c includes the set screw 172 of FIGS. 13 and 14 in place between the two threaded grooves 164, 166. In the embodiment shown in FIGS. 15a and c, the disc insert 134 was removed prior to insertion of the set screw. However, it is possible to leave the disc insert in place. Also, it should be noted that the cups in FIG. 12 could also have been removed (i.e. unscrewed) or lowered prior to inserting the set screw. Although both cups are adjustably mounted to the base plates in FIGS. 12 and 15, it is also possible for one or both of the cups to be fixedly mounted to or simply defined by the interior surface of the base plates. The prosthesis assembly of FIG. 12 also includes two "stops." The first stop 174 is attached to the circumferential edge 160 of the superior base plate 130 and the second stop 176 is attached to the circumferential edge 162 of the inferior base plate 106. In the embodiment shown, these stops, which are designed to prevent the set screw from slipping out, take the form of thin, flexible wires that stick out over or into the threaded grooves. FIG. 15b shows a close up view of an illustrative recoil wire 176 that is inset into the circumferential edge 162 of the inferior base plate 106. The wires flex away from the groove as a set screw is screwed into place, allowing the set screw to be inserted into the groove unhindered, however, once the set screw is fully inserted and the face of the set screw is flush with the circumferential edge of the base plates, the wires recoil back over or into the groove, preventing the set screw from becoming dislodged. The recoil wires may be attached to the circumferential edge of the base plates, as shown in the figure, or may be inset slightly into the threaded groove. Although only two stops are shown in FIG. 12, more than two stops may be used and these may be positioned at a variety of locations around the threaded grooves.

Figure 19A:
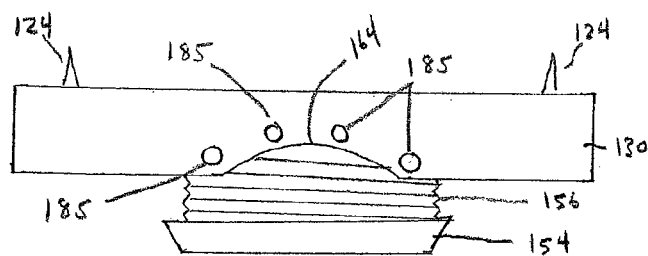
FIG. 19a shows a front view of the disc prosthesis of FIG. 12 without the disc insert. The base plates include screw holes to allow attachment of a set screw.
Figure 19A:
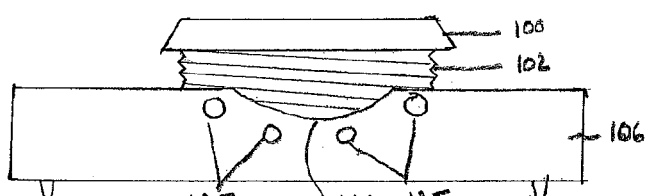
Figure 19A:
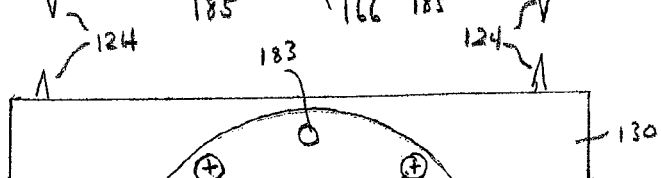
Figure 19:
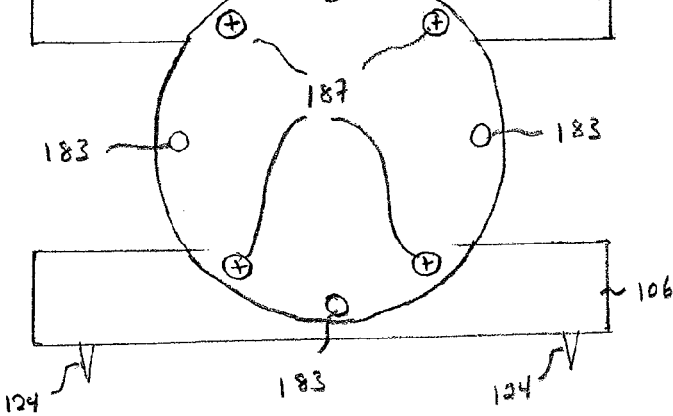
FIG. 19b shows a front view of the disc prosthesis of FIG. 19a with the set screw of FIG. 18 in place.
Figure 18:
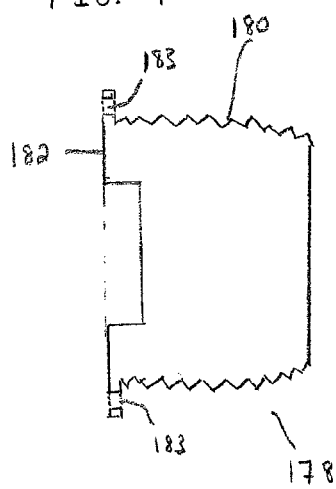
FIG. 18 shows a cross-sectional side view of a set screw that may be used to immobilize the disc prosthesis of FIG. 12.

In an alternative design, the set screw may have a head that includes one or more screw apertures extending through its top face. These apertures may be aligned with tapped bores in the base plates and screws may be inserted through the apertures into the tapped bores in order to secure the set screw to the base plates. A cross-sectional view of a set screw that may be used in this manner is shown in FIG. 18. As shown in the figure, the set screw 178 includes a tapered threaded body 180 and a flat face 182 having a plurality of screw apertures 183. The number and spacing of the apertures is not critical, provided at least one aperture may be lined up with at least one opposing tapped bore in a base plate when the set screw is in place. FIG. 19a shows a disc prosthesis having tapped bores 185 in its superior 130 and inferior base plates 106 and FIG. 19b shows the disc prosthesis of FIG. 19a with the set screw 178 of FIG. 18 secured by four screws 187 to its superior and inferior base plates.

In an alternative embodiment, the apertures in the face of the set screw may be positioned such that a bone screw may be inserted through one or more of the apertures and into a vertebra when the disc prosthesis is in place. In this embodiment, the face of the set screw should have a diameter large enough to position the screw apertures over the vertebra when the disc prosthesis is in place. Alternatively, the face of the set screw may include tabs that extend outwardly from the face of the set screw and overlap with the vertebra when the disc prosthesis is in place, allowing bone screws to be inserted through screw apertures in the tabs and into the vertebra.

Figure 20:
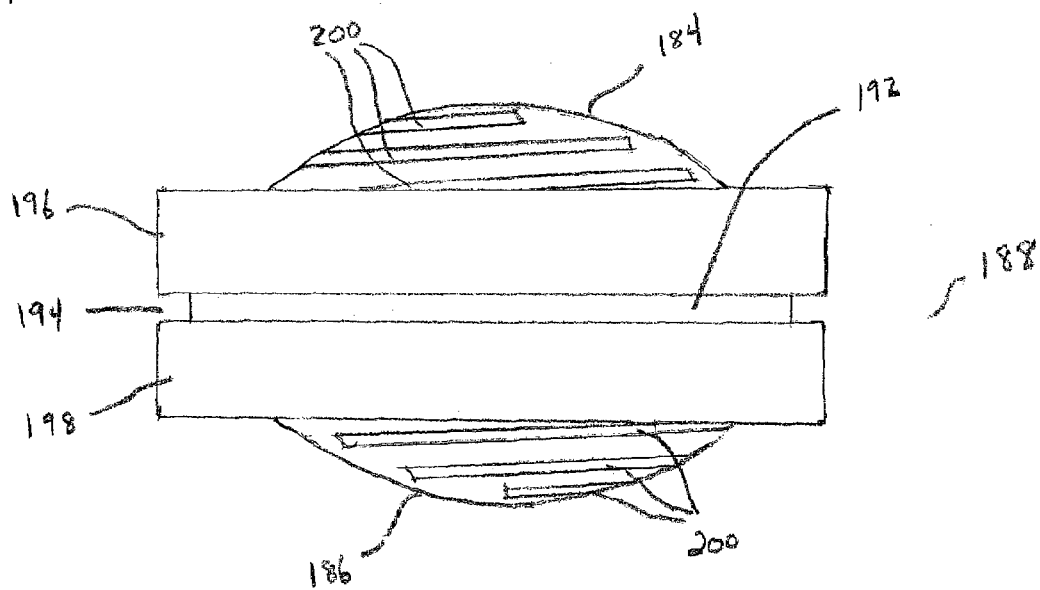
FIG. 20 shows a front view of a disc insert that may be used with the disc prostheses of FIG. 9 or 12.
Figure 21:
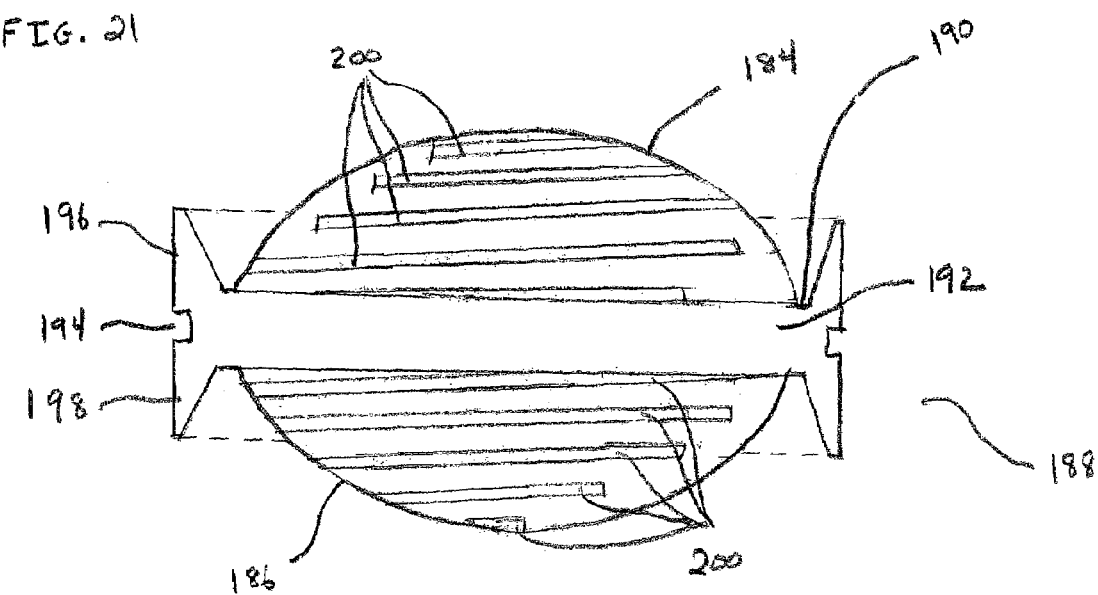
FIG. 21 shows a cross-sectional view of a disc insert that may be used with the disc prostheses of FIG. 9 or 12.

FIG. 20 shows a front view of a disc insert that may be used, for example, with a disc prosthesis of the type shown in FIG. 9 or FIG. 12. FIG. 21 shows a cross-sectional view of the disc insert. This insert allows for axial loading, to provide a more natural range of motion. The disc insert includes a first convex surface 184, a second convex surface 186, and a central collar 188. The collar extends through the disc insert and includes a flat ring portion 190 and an outer circumferential wall 192 having a circumferential groove 194 that separates the outer circumferential wall into an upper rim 196 and a lower rim 198. The two convex surfaces are formed by a wall having a plurality of compressible helical slits 200 defined therein. As shown in the figures, the slits are desirably disposed on the convex surfaces in at least partial overlapping relation. The slits are compressible, such that forces exerted by vertebrae on a disc prosthesis that includes the disc insert, are transferred along the convex surfaces through the overlapping region, providing a spring-like characteristic.

FIGS. 22-24 show some optional features of the disc prostheses that may help to more accurately mimic the natural motions of an intervertebral disc. FIG. 22 shows a side view of the disc prosthesis of FIG. 12, including two elastic cables 202, 204 connected between the superior base plate 130 and the inferior base plate 106. These cables are used to restrict the rotational motion of the base plates. In FIG. 22 the cables are depicted running substantially parallel. FIG. 23 shows an alternative cable arrangement where the cables 206, 208 criss-cross. In both configurations, the disc prosthesis may include a second pair of cables (not shown) disposed symmetrically on the other side of the prosthesis. If the superior base plate 130 is viewed from above as a twelve hour clock face with the twelve o'clock position corresponding to the most posterior point of the plate in FIGS. 22 and 23, the cables are secured to the base plates at approximately the 2:00 and 4:00 positions and a symmetrically disposed pair of cables on the other side of the prosthesis would be secured at approximately the 8:00 and 10:00 positions. However, these positions are not critical and it should be understood that the cables may be secured at other positions.

FIG. 24 shows a cross-sectional side view of an assembly including a cup 210 adjustably mounted to a base plate 212 via a threaded stem 214. This assembly is similar to that shown in FIG. 1, with the exception that the cup 210 of FIG. 24 includes a flat strip 216 running through the center of the concave surface 218 in a direction substantially perpendicular to the anterior-posterior axis of the base plate. When the assembly is incorporated into a ball-in-socket type disc prosthesis, the convex surface which engages the cup is able to translate along the strip. This design may be used to more accurately mimic the natural motion of an intervertebral disc.

Figure 25:
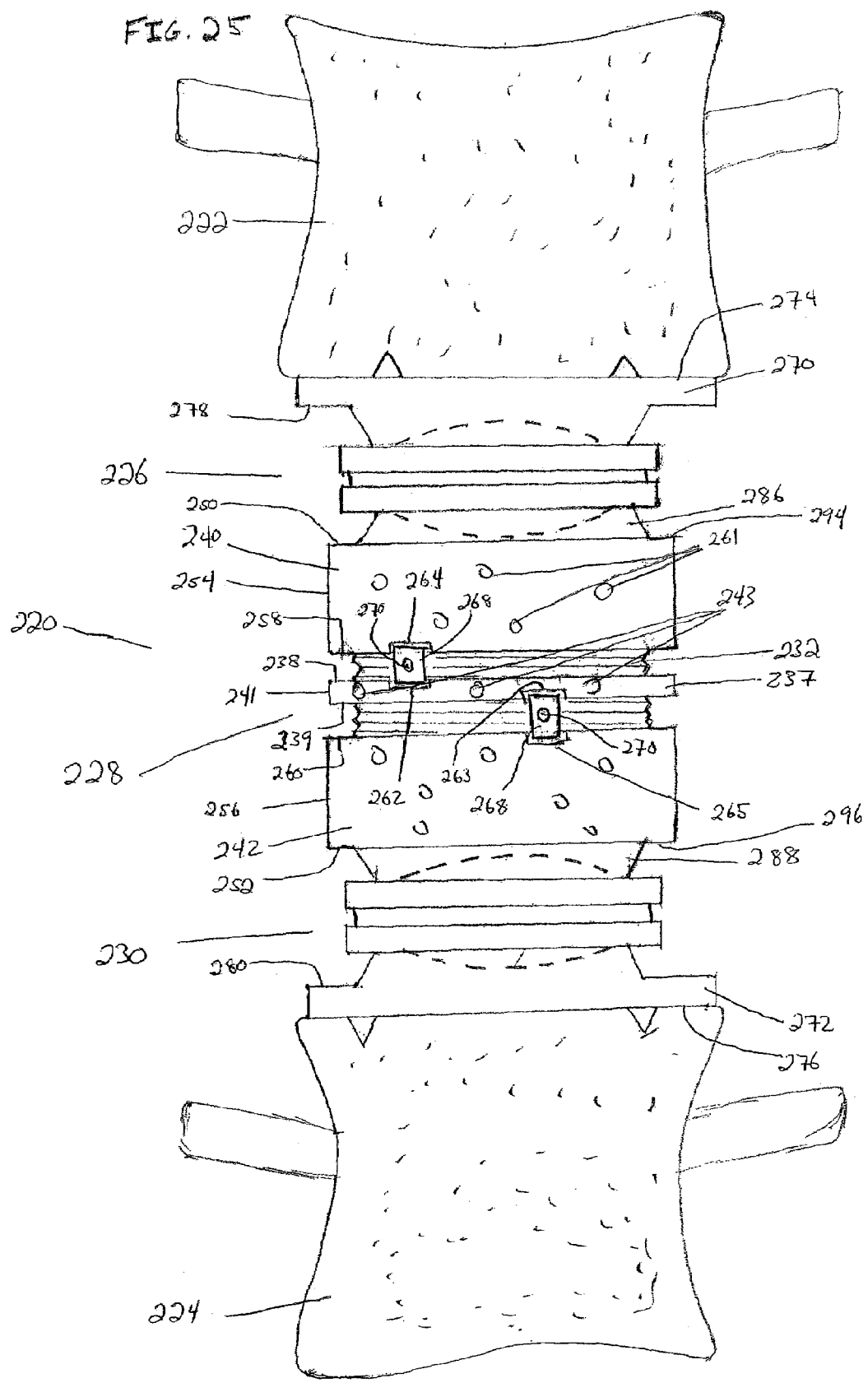
FIG. 25 shows a front view of a prosthetic vertebral assembly implanted between a superior vertebra and an inferior vertebra.
Figure 26:
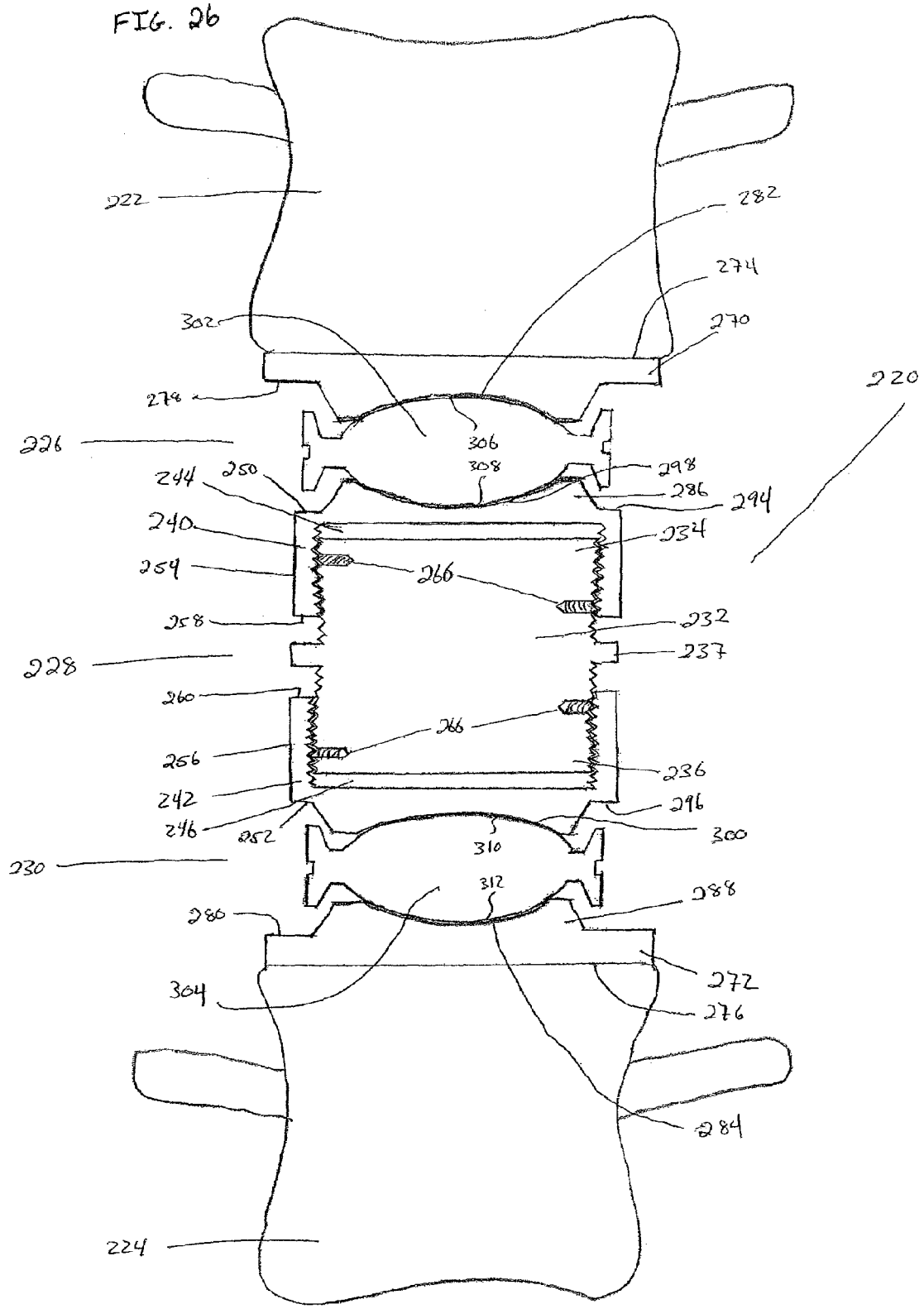
FIG. 26 shows a cross-sectional front view of the prosthetic vertebral assembly of FIG. 25.
Figure 27:
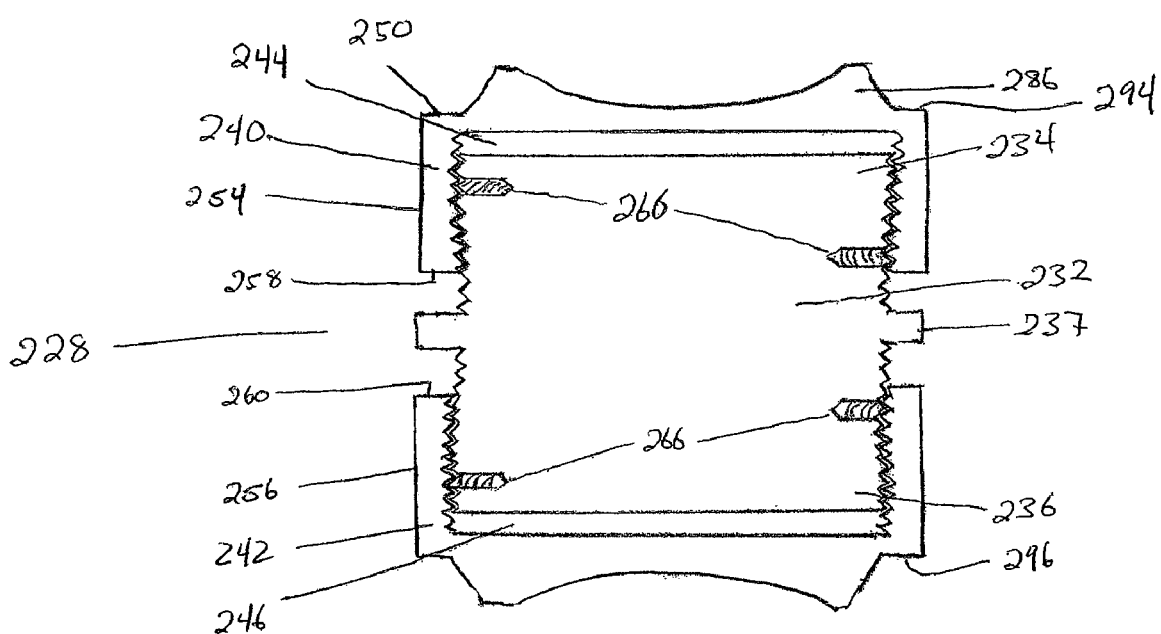
FIG. 27 shows a cross-sectional view of the prosthetic vertebral body of the prosthetic vertebral assembly of FIG. 25.

A prosthetic vertebral assembly is shown in FIGS. 25 and 26. FIG. 25 shows a front view of the prosthetic vertebral assembly 220 implanted between a superior vertebra 222 and an inferior vertebra 224. FIG. 26 shows a cross-sectional front view of the assembly. The prosthetic vertebral body includes a first intervertebral disc prosthesis 226, a prosthetic vertebral body 228 and a second intervertebral disc prosthesis 230. FIGS. 27 and 28 show a cross-sectional and front view, respectively, of the prosthetic vertebral body 228. The base of the prosthetic vertebral body in this embodiment is composed of a threaded rod 232 characterized by a superior end 234 and an inferior end 236. The threaded rod optionally includes a central collar 237 characterized by an upper 238 surface, a lower surface 239 and a circumferential edge 241. One or more holes 243 adapted to engage with a tool that grips and rotates, or grips and immobilizes, the threaded rod extend into the circumferential edge of the collar. Although the rod depicted in the figures is a solid cylinder, it should be understood that the rod may also be hollow.

A superior vertically adjustable support 240 is adjustably mounted to the superior end of the threaded rod and an inferior vertically adjustable support 242 is adjustably mounted to the inferior end of the threaded rod. The superior vertically adjustable support defines a first tapped bore 244 extending into one surface thereof and the inferior vertically adjustable support defines a second tapped bore 246 extending into one surface thereof. The superior and inferior vertically adjustable supports are each characterized by an exterior surface 250, 252 that faces toward a vertebra when the prosthetic vertebral body is implanted in a patient's spine, a circumferential edge 254, 256 and an interior surface 258, 260 that faces toward the intervertebral space when the prosthetic vertebral body is implanted in patient's spine. Like the collar on the threaded rod, the circumferential edges of the adjustable supports may optionally include one or more holes 261 adapted to engage with a tool that grips and rotates, or grips and immobilizes, the adjustable supports.

The prosthetic vertebral body depicted in FIGS. 25 and 26 show an example of a mechanism that may be used to lock in the height of the body once it has been properly adjusted. This mechanism is analogous to that depicted in FIG. 4, above. In this design, both the superior and inferior vertically adjustable supports include one or more notches 264, 265 cut into their circumferential edges 254, 256 along their interior surfaces 258, 260. The central collar 237 of the threaded rod includes one or more notches 262 cut into its circumferential edge 241 along its upper surface 238 and one or more notches 263 cut into its circumferential edge 241 along its lower surface 239. A plurality of tapped holes 266 extend radially into the threaded rod above and below the central collar 237. As the superior and inferior vertically adjustable supports are rotated outwardly from a position where they rest against the collar, the tapped holes in the threaded rod become exposed. The tapped holes are vertically displaced from one another around the circumference of the threaded rod, such that more threaded holes are exposed as the superior and inferior vertically adjustable supports are rotated away from the collar. For example, the tapped holes may be displaced such that one additional tapped hole becomes exposed every time an adjustable support is rotated outwardly by an additional 1 millimeter. However, other displacements are possible.

FIGS. 25 and 26 show how the notches in the vertically adjustable supports and the collar of the threaded rod may be used to lock in the height of the prosthetic vertebral body once it has been properly adjusted. When a notch on a vertically adjustable support is lined up opposite and facing a notch on the collar, the pair of notches form a frame into which a tab 268, such as that shown in FIGS. 5-7, may be fastened against the threaded rod using a screw 270 that engages one of the tapped holes 266 extending radially into the threaded rod. When the tabs 268 are in place, the vertically adjustable supports 240, 242 are unable to rotate with respect to the collar 237. The screws 270 may be aligned at a substantially right angle with respect to the long axis of the threaded rod 232, or may be aligned at a different angle to make it more accessible in situ. The contour of the inner surfaces of the tabs 268 may be designed to match the contour of the outer surface of the threaded rod 232 to provide a snug fit when the tab is screwed into place. Although the tab and frame in FIGS. 25 and 26 are generally rectangular in shape, it should be understood that a variety of alternative shapes may also be employed.

In the exemplary embodiment depicted in FIGS. 25 and 26, the first and second disc prostheses 226, 230 each includes a first base plate 270, 272 characterized by an exterior surface 274, 276 and an interior surface 278, 280 that defines a concave surface 282, 284. The disc prostheses further include a second base plate 286, 288 that is integrated with the one of the vertically adjustable supports 240, 242 of the prosthetic vertebral body 228. The second base plate 286, 288 is also characterized by an interior surface 294, 296 that defines a concave surface 298, 300. The concave surfaces of the first and second base plates are disposed opposite one another in a substantially parallel relation, such that the concave surfaces of the first and second base plates are disposed opposite and facing one another. The disc prostheses each also include a disc insert 302, 304 having two opposing convex surfaces 306, 308 and 310, 312 disposed between and in contact with the two opposing concave surfaces of the base plates. Each of the first base plates includes a plurality of pins 310 on its exterior surface for attaching the base plates to the superior and inferior vertebrae.

The invention has been described with reference to specific illustrative embodiments. However it should be understood that many variations and modifications may be made while remaining within the spirit and scope of the invention.

What is claimed is:

1. An intervertebral disc prosthesis assembly comprising:
   (a) a first base plate comprising a circumferential edge, an interior surface, an exterior surface and a first threaded groove extending into the circumferential edge along the interior surface;
   (b) a second base plate disposed opposite the first base plate, the second base plate comprising a circumferential edge, an interior surface, an exterior surface, and a second threaded groove extending into the circumferential edge along the interior surface, the second threaded groove disposed opposite and facing the first threaded groove; and
   (c) a threaded rod that engages the first and second threaded grooves of the first and second base plates;
   wherein the interior surface of the first base plate has a first cup disposed thereon, the first cup defining a first concave surface, and the interior surface of the second base plate has a second cup disposed thereon, the second cup defining a second concave surface, and further wherein the disc prosthesis system further comprises a disc insert comprising two opposing convex surfaces disposed between the first and second concave surfaces.

2. The intervertebral disc prosthesis assembly of claim 1, further comprising a joint disposed between the first and second base plates.

3. The intervertebral disc prosthesis assembly of claim 1, wherein the interior surface of either the first or second base plate has a cup disposed thereon, the cup defining a concave surface, and the other interior surface has a knob disposed thereon, the knob defining a convex surface, wherein the concave surface of the cup and the convex surface of the knob fit together to form an articulating joint.

4. The intervertebral disc prosthesis assembly of claim 1, wherein the threaded rod comprises a face defining at least one aperture that extends over the circumferential edge of the first or second base plate and at least one of the first or second base plates comprises a tapped hole along its circumferential edge that may be aligned with the at least one aperture.

5. The intervertebral disc prosthesis assembly of claim 1, wherein the threaded rod comprises a face defining at least one aperture that extends over a vertebra when the disc prosthesis assembly is in place in an intervertebral space.

6. The intervertebral disc prosthesis assembly of claim 1, wherein:
   the disc insert further comprises an exterior wall forming the two opposing convex surfaces capable of articulating with the first and second concave surfaces of the base plates, wherein the exterior wall defines a plurality of compressible helical slits.

7. The intervertebral disc prosthesis of claim 6, wherein the plurality of helical slits are disposed in a substantially parallel relation.

* * * * *